(12) United States Patent
Hayashi

(10) Patent No.: US 6,961,406 B2
(45) Date of Patent: Nov. 1, 2005

(54) X-RAY DIAGNOSTIC APPARATUS

(75) Inventor: Takashi Hayashi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/687,606

(22) Filed: Oct. 20, 2003

(65) Prior Publication Data
US 2004/0081271 A1 Apr. 29, 2004

Related U.S. Application Data

(63) Continuation of application No. PCT/JP02/08417, filed on Aug. 21, 2002.

(30) Foreign Application Priority Data

Sep. 17, 2001 (JP) ........................................ 2001-282256

(51) Int. Cl.[7] ................................................ H05G 1/64
(52) U.S. Cl. .................................................... 378/98.12
(58) Field of Search ..................................... 378/98.12

(56) References Cited

U.S. PATENT DOCUMENTS 4,613,983 A * 9/1986 Yedid et al. .............. 378/98.12
5,631,942 A * 5/1997 Shinoda .................... 378/98.12

FOREIGN PATENT DOCUMENTS

| JP | 62-268535 | 11/1987 |
|---|---|---|
| JP | 6-70924 | 3/1994 |
| JP | 6-165035 | 6/1994 |

* cited by examiner

Primary Examiner—Craig E. Church
(74) Attorney, Agent, or Firm—Oblon, Spivak, McClelland, Maier & Neustadt, P.C.

(57) ABSTRACT

A diagnostic X-ray system includes an imaging system that generates image data sets from shots by subjecting a patient to X-ray exposure, a supporting mechanism that supports the imaging system movably with respect to the patient, a system controller that controls the imaging system and the supporting mechanism in such a manner that shots are repeated at each of a plurality of shot positions set discretely along the body axis of the patient, and an image processing apparatus that generates another image data set covering a range wider than the field of view of the imaging system from the image data sets.

14 Claims, 14 Drawing Sheets

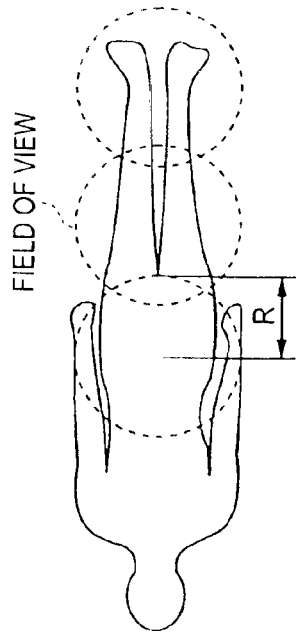
FIG. 4A
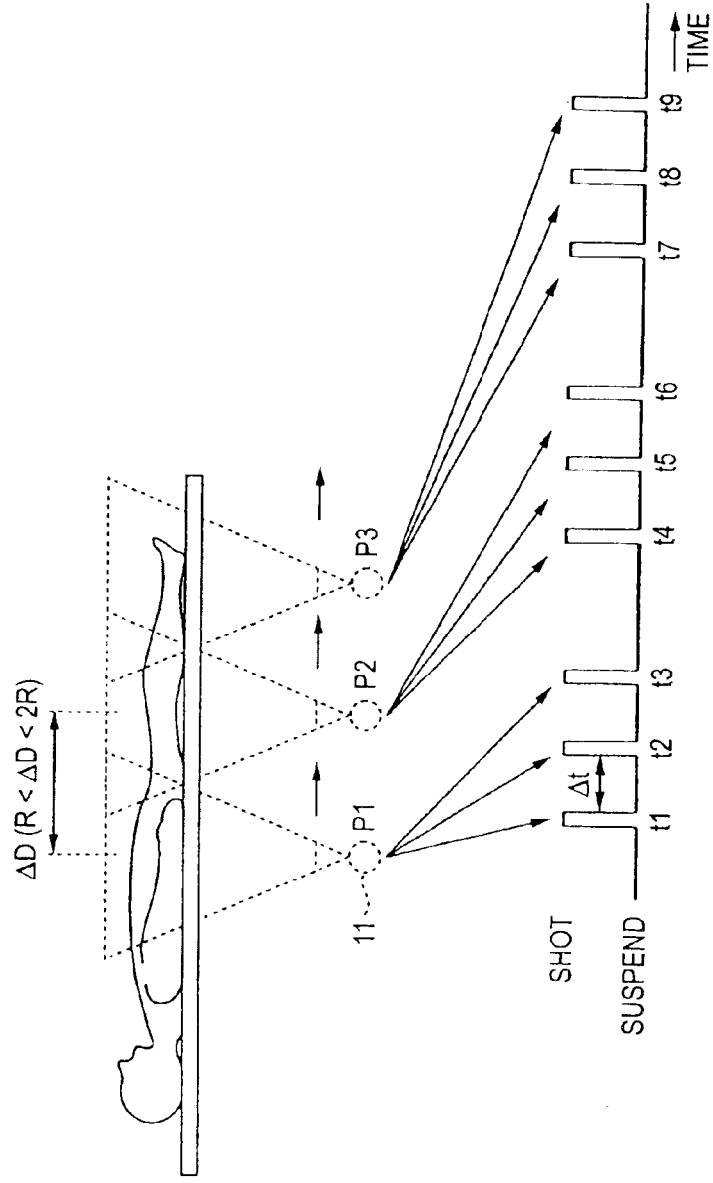
FIG. 4B
FIG. 4C

X-RAY DIAGNOSTIC APPARATUS

CROSS-REFERENCE TO RELATED APPLICATIONS

This is a Continuation Application of PCT Application No. PCT/JP02/08417, filed Aug. 21, 2002, which was not published under PCT Article 21(2) in English.

This application is based upon and claims the benefit of priority from the prior Japanese Patent Applications No. 2001-282256, filed Sep. 17, 2002, the entire contents of which are incorporated herein by reference.

BACKGROUND OF THE INVENTION

1. Field of the Invention

The present invention relates to an X-ray diagnostic apparatus that takes a shot by subjecting a patient to X-ray exposure.

2. Description of the Related Art

An imaging system includes an X-ray tube and an imaging device. Most of today's imaging devices include an image intensifier and a TV camera. An imaging device adopting a flat panel detector equipped with a solid-state image sensor is expected to come into widespread use in the near feature. The field of view of the imaging system is limited to the field of view of the imaging device.

There is a shoot technique to obtain an image of a range wider than the limited field of view of the imaging system. This shoot technique includes an intermittent movement shoot method in which the imaging system moves intermittently, and a continuous movement shoot method in which the imaging system moves continuously. In either shoot method, shots are repeated in association with the movement of the imaging system. A plurality of images generated through repetitive shots are jointed according to their respective shot positions. An image covering a range wider than the field of view of the imaging system is thus generated.

Stepping DSA (Digital Subtraction Angiography) is known as a typical example of the intermittent movement shoot method. Bolus DSA is known as a typical example of the continuous movement shoot method.

A contrast medium injected into a patient moves on the flow of blood. The imaging system is moved either intermittently or continuously to chase the moving contrast medium. As shown in FIG. 14, shots are repeated while the imaging system is kept moved.

A plurality of images generated through repetitive shots are subtracted from mask images at the respective corresponding shot positions. A plurality of subtraction images are then jointed according to their respective shot positions. A blood vessel extracted image corresponding to a wide range is thus generated.

According to the bolus DSA, a contrast medium of a high concentration is injected into a patient in an extremely short time. The contrast medium of a high concentration injected into the patient by the bolus injection method moves within blood vessels of the patient as a bolus. The imaging system repeats shots while chasing the contrast medium that is moving as a bolus.

The contrast medium injected into the patient starts to diffuse with time and is diluted little by little. A diluted contrast medium gives rise to deterioration in the ability to extract blood vessels. The bolus DSA method has an advantage in suppressing the deterioration of the blood vessel extracting ability.

According to the bolus DSA method, movements of the imaging system and shot triggers are often manipulated manually by a radiographer. The radiographer predicts the flow of blood and moves the imaging system to determine the timing of a shot trigger. The flow of blood differs from patient to patient and from region to region. Further, the flow of blood varies even in the same region of the same patient. Hence, not only a high degree of concentration and attention, but also considerably high skills are needed for the moving manipulation of the imaging system and the shot trigger manipulation.

The contrast medium does not necessarily flow in the blood vessels in the form of a perfect bolus even when it is injected by the bolus injection method. The contrast medium starts to diffuse little by little with time, and it cannot be avoided that a concentration of the contrast medium is lowered little by little with time due to diffusion. This, on rare occasion, causes an unwanted event that the contrast of the contrast medium becomes too low for use in diagnosis.

BRIEF SUMMARY OF THE INVENTION

It is therefore an object of the invention to provide a diagnostic X-ray system that can tolerate a delay in shot timing.

A first aspect of the invention provides an X-ray diagnostic apparatus, including: an imaging system that generates image data sets from shots by subjecting a patient to X-ray exposure; a supporting mechanism that supports the imaging system in such a manner so as to be allowed to move relatively with respect to the patient; a system controller that controls the imaging system and the supporting mechanism in such a manner that shots are repeated at each of a plurality of shot positions set discretely along a body axis of the patient; and an image processing portion that generates a given image data set covering a range wider than a field of view of the imaging system from the image data sets.

A second aspect of the invention provides an X-ray diagnostic apparatus, including: an imaging system that generates image data sets from shots by subjecting a patient to X-ray exposure; a supporting mechanism that supports the imaging system in such a manner so as to be allowed to move relatively with respect to the patient; a system controller that controls the supporting mechanism in such a manner that the imaging system is repetitively moved and suspended in turn along a body axis of the patient, and controls the imaging system in such a manner that shots are repeated at each suspended position; and an image processing portion that generates a given image data set covering a range wider than a field of view of the imaging system from the image data sets.

A third aspect of the invention provides an X-ray diagnostic apparatus, including: an imaging system that generates image data sets from shots by subjecting a patient to X-ray exposure; a supporting mechanism that supports the imaging system in such a manner so as to be allowed to move relatively with respect to the patient; a system controller that controls the imaging system and the supporting mechanism so as to generate a plurality of first image data sets at different shot times, all corresponding to a first shot position, and a plurality of second image data sets at different shot times, all corresponding to a second shot position; and an image processing portion that generates a single third image data set covering a range wider than a field of view of the imaging system from the first and second image data sets.

BRIEF DESCRIPTION OF THE SEVERAL VIEWS OF THE DRAWING

FIG. 4A, FIG. 4B, and FIG. 4C are supplementary views of FIG. 3;

DETAILED DESCRIPTION OF THE INVENTION

The following description will describe a preferred embodiment of an X-ray diagnostic apparatus of the invention with reference to the drawings.

Figure 1:
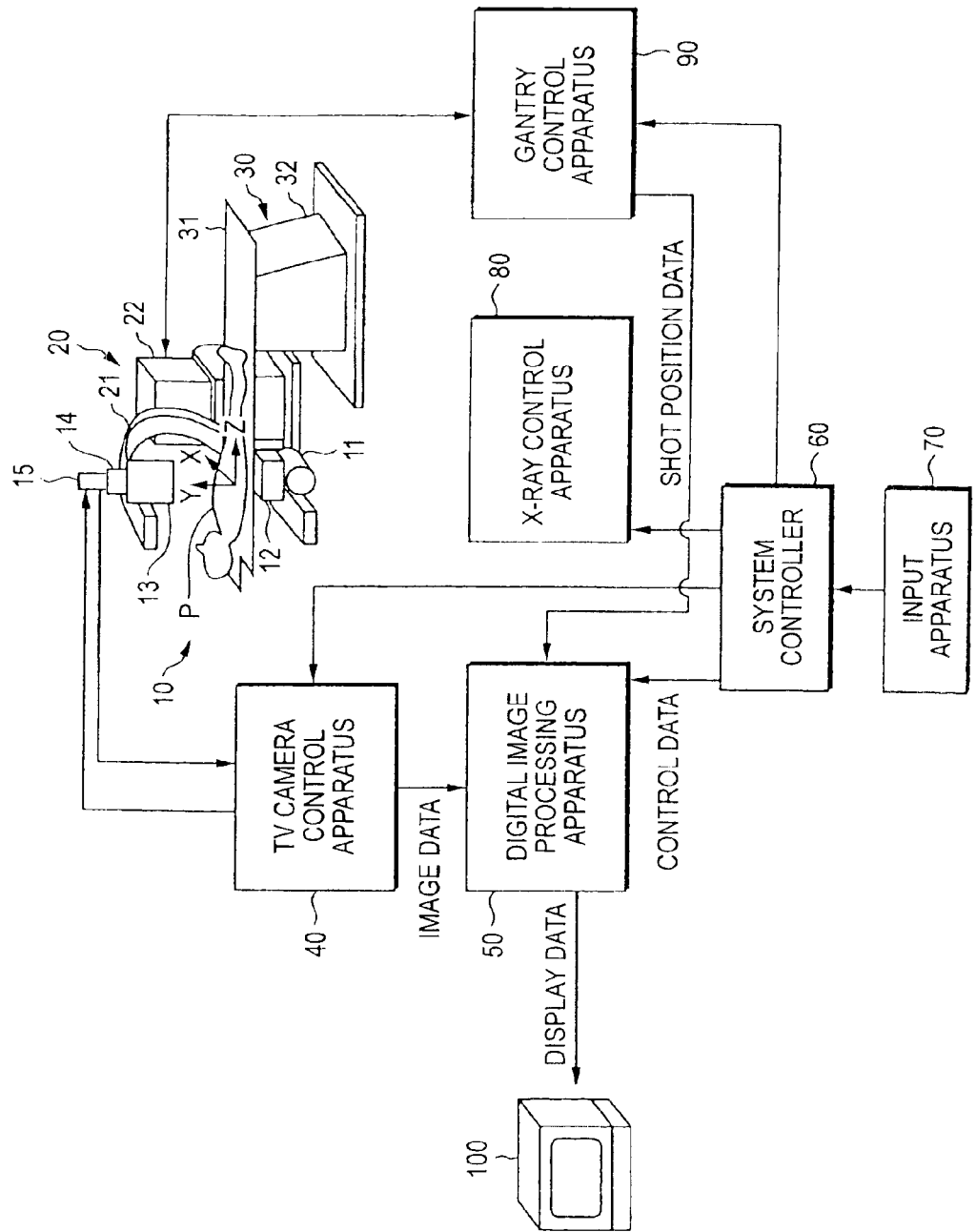
FIG. 1 is a view showing an arrangement of a major portion in an X-ray diagnostic apparatus according to one embodiment of the invention.
Figure 2:
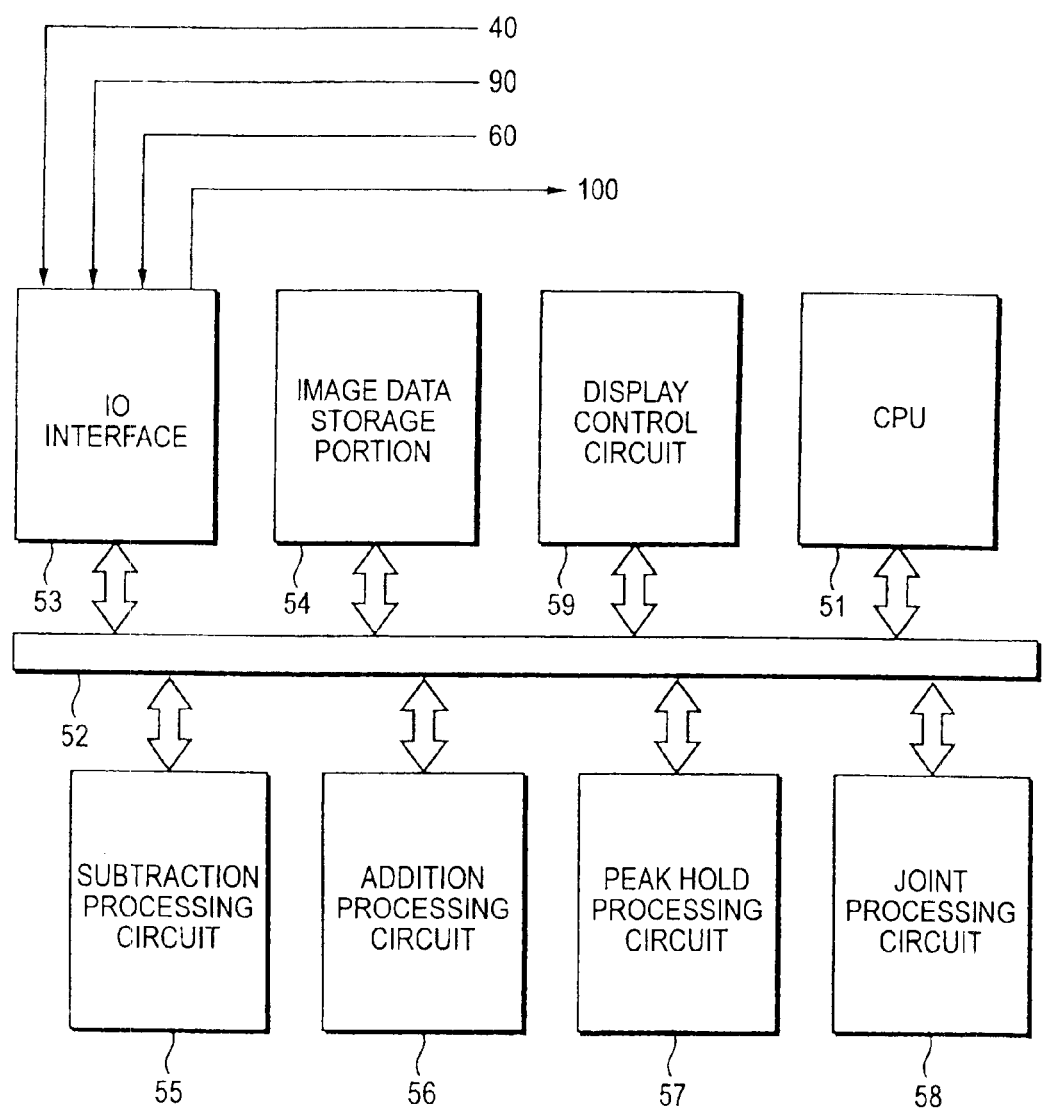
FIG. 2 is a view showing an arrangement of a digital image processing apparatus of FIG. 1.

FIG. 1 is a view depicting an arrangement of an X-ray diagnostic apparatus according to one embodiment of the invention. FIG. 2 is a block diagram of a digital image processing apparatus of FIG. 1. An imaging system 10 generates image data sets from shots by subjecting a patient to X-ray exposure. The imaging system 10 includes an X-ray tube 11 and an imaging device. An X-ray collimator 12 is attached to the X-ray tube 11. The imaging device comprises an image intensifier 13, an optical system 14, and a TV camera 15. The imaging device may comprise a flat panel detector adopting a solid-state image sensor. The solid-state image sensor comprises, for example, a semiconductor layer made of selenium or the like, a voltage applying electrode formed on the surface of the semiconductor layer, and a signal electrode formed on the back surface of the semiconductor layer. As is known, the detection principle is as follows: electron-hole pairs are generated by ionization that takes place when an X-ray is incident on the semiconductor layer, and attracted respectively to reverse-biased electrodes, whereby a signal current corresponding to the strength of the incident X-ray is generated. The solid-state image sensor may be a combination of a scintillator and a photo-diode.

The imaging system 10 is supported movably by a supporting mechanism 20. The supporting mechanism 20 includes a C-arm 21. The X-ray tube 11 and the imaging device are mounted on the C-arm 21. An arm stand 22 is equipped with a mechanism that supports the C-arm 21 movably with respect to the body axis (Z-axis) of the patient P, an electric motor for movement drive, and a position sensor, such as a rotary encoder, that detects the position of the C-arm 21.

A diagnostic table 30 comprises a table top 31 on which the patient P lies down, and a stand 32 that supports the table top 31 movably with respect to all the X-, Y-, and Z-axes.

The X-ray tube 11 exposes X-rays upon application of a tube voltage and upon supply of a filament current from an X-ray control apparatus 80. The X-rays are shaped into beams having an arbitrary diameter by the collimator 12 and then radiated to the patient P lying on the diagnostic table 30. The X-rays having passed through the patient P are converted into an optical image in the image intensifier 13. The optical image is then formed on an image screen of the TV camera 15 through the optical system 14 equipped with an iris, and converted into an electrical signal in the TV camera 15.

An image signal generated in the TV camera 15 is amplified in a TV camera control apparatus 40, converted into a digital signal, and outputted to the digital image processing apparatus 50 as an image data set.

As shown in FIG. 2, the digital image processing apparatus 50 is provided with a CPU 51 as a control center. An input/output interface (IO I/F) 53, an image data set storage portion 54, a subtraction processing circuit 55, an addition processing circuit 56, a peak hold processing circuit 57, a joint processing circuit 58, and a display control circuit 59 are connected to the CPU 51 by way of a data set/control bus 52.

The subtraction processing circuit 55 is provided to generate blood vessel enhanced image data sets in which images of blood vessels are enhanced or blood vessel extracted image data sets in which images of blood vessels are extracted, by subtracting pre-contrast image data sets (referred to as mask images) from post-contrast image data sets (referred to as original images or live images) under the control of the CPU 51. The subtraction processing may be replaced with threshold value processing to generate the blood vessel enhanced image data sets or the blood vessel extracted image data sets in which images of blood vessels are extracted.

The addition processing circuit 56 is provided to generate addition image data sets by adding up a plurality of blood vessel extracted image data sets (subtraction image data sets) at the same shot position and at different shot times between frames under the control of the CPU 51.

The peak hold processing circuit 57 is provided to generate peak hold image data sets from a predetermine number of blood vessel extracted image data sets (subtraction image data sets) at the same shot position and at different shot times under the control of the CPU 51. It should be noted that the addition processing circuit 56 and the peak hold processing circuit 57 are used selectively.

The joint processing circuit 58 is provided to generate a single joint image data set by jointing a plurality of addition image data sets or a plurality of peak hold image data sets at different shot positions according to the shot positions under the control of the CPU 51.

The display control circuit 59 is provided to generate display data sets from the original image data sets, the subtraction image data sets, the addition image data sets, the peak hold image data sets, or the joint image data sets under the control of the CPU 51.

A system controller 60 controls the X-ray control apparatus 80, a gantry control apparatus 90, the TV camera control apparatus 40, and the digital image processing apparatus 50 to manage operations related to shots, image processing, and display. An input apparatus 70 including a keyboard, a mouse, a touch panel, etc. is connected to the system controller 60, and various settings for operations, such as shot conditions and display conditions, can be set through the input apparatus 70.

A shoot operation according to this embodiment will now be explained.

Figure 3:
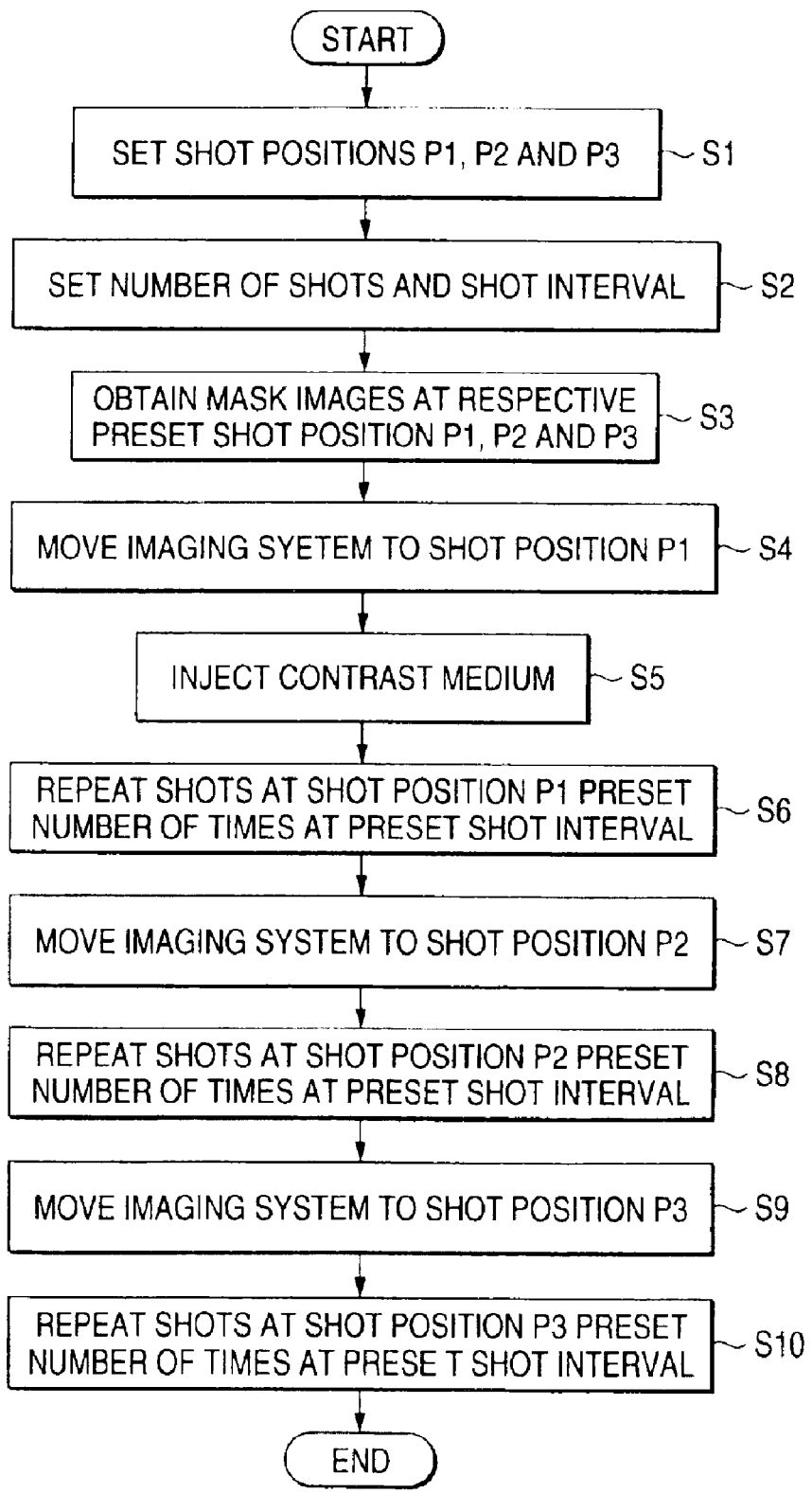
FIG. 3 is a flowchart detailing a shoot operation in the embodiment.
Figure 5:
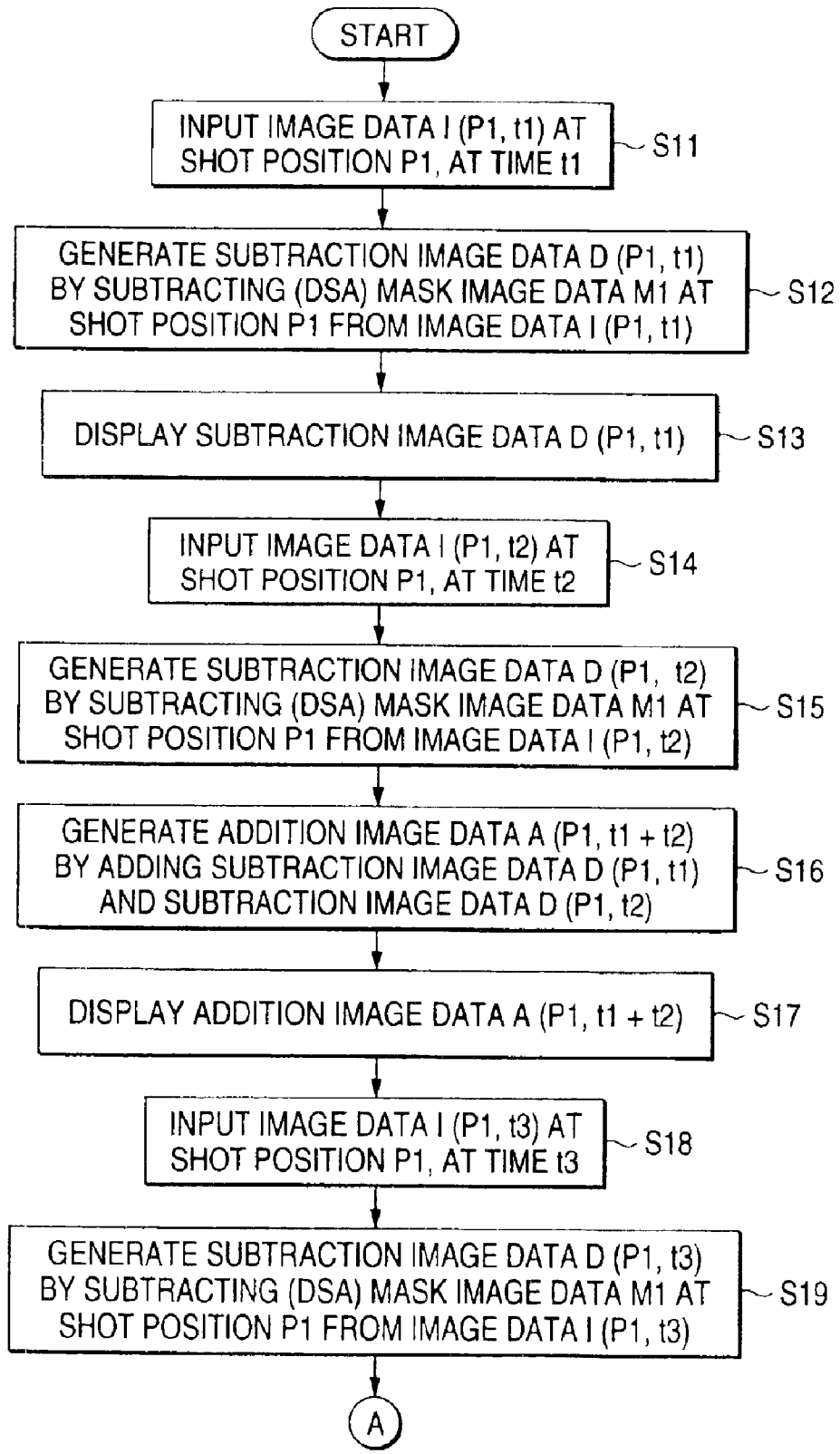
FIG. 5 is a flowchart showing a procedure of processing by the digital image processing apparatus of FIG. 1.
Figure 6:
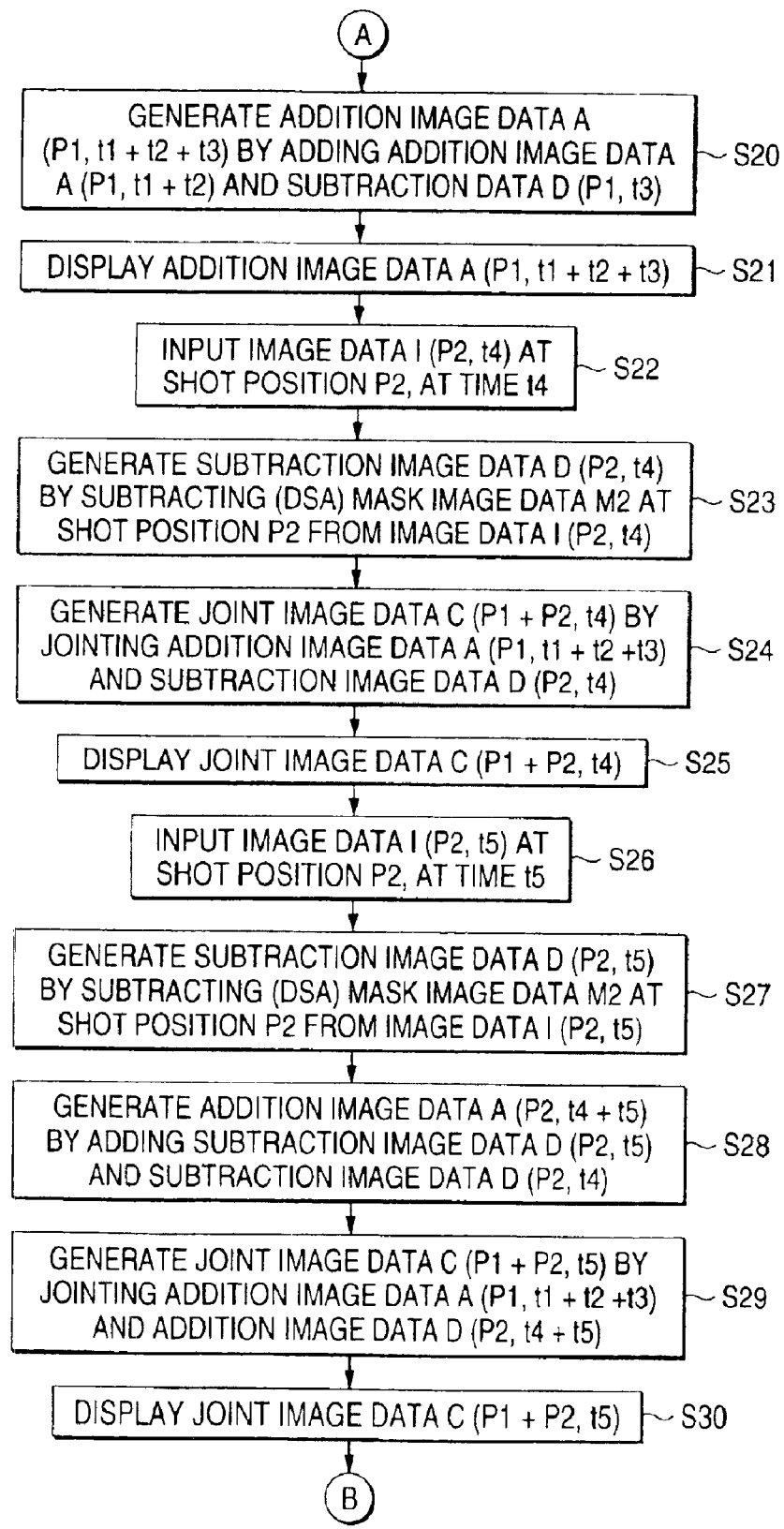
FIG. 6 is a flowchart continuing from FIG. 5.
Figure 7:
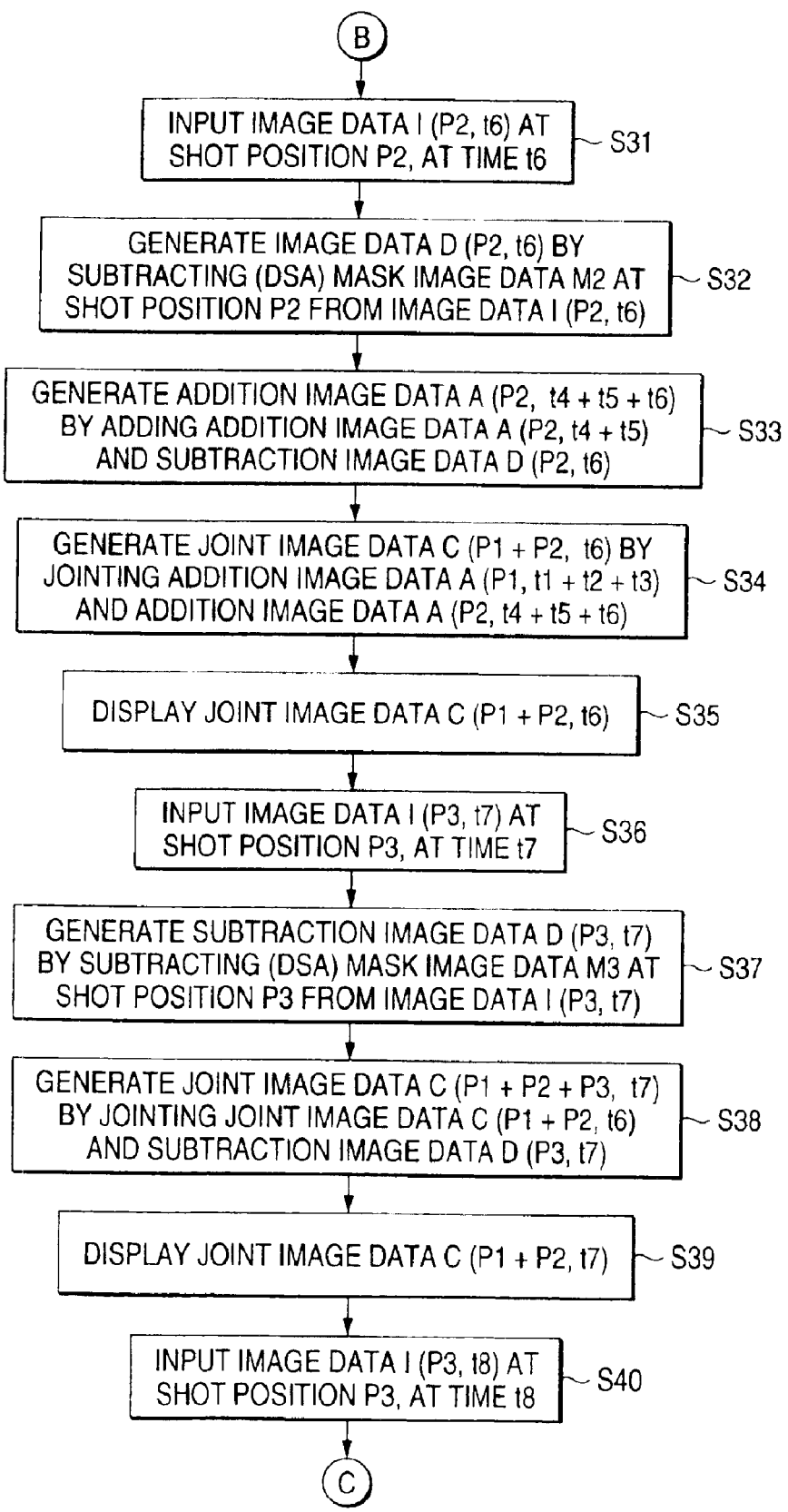
FIG. 7 is a flowchart continuing from FIG. 6.
Figure 8:
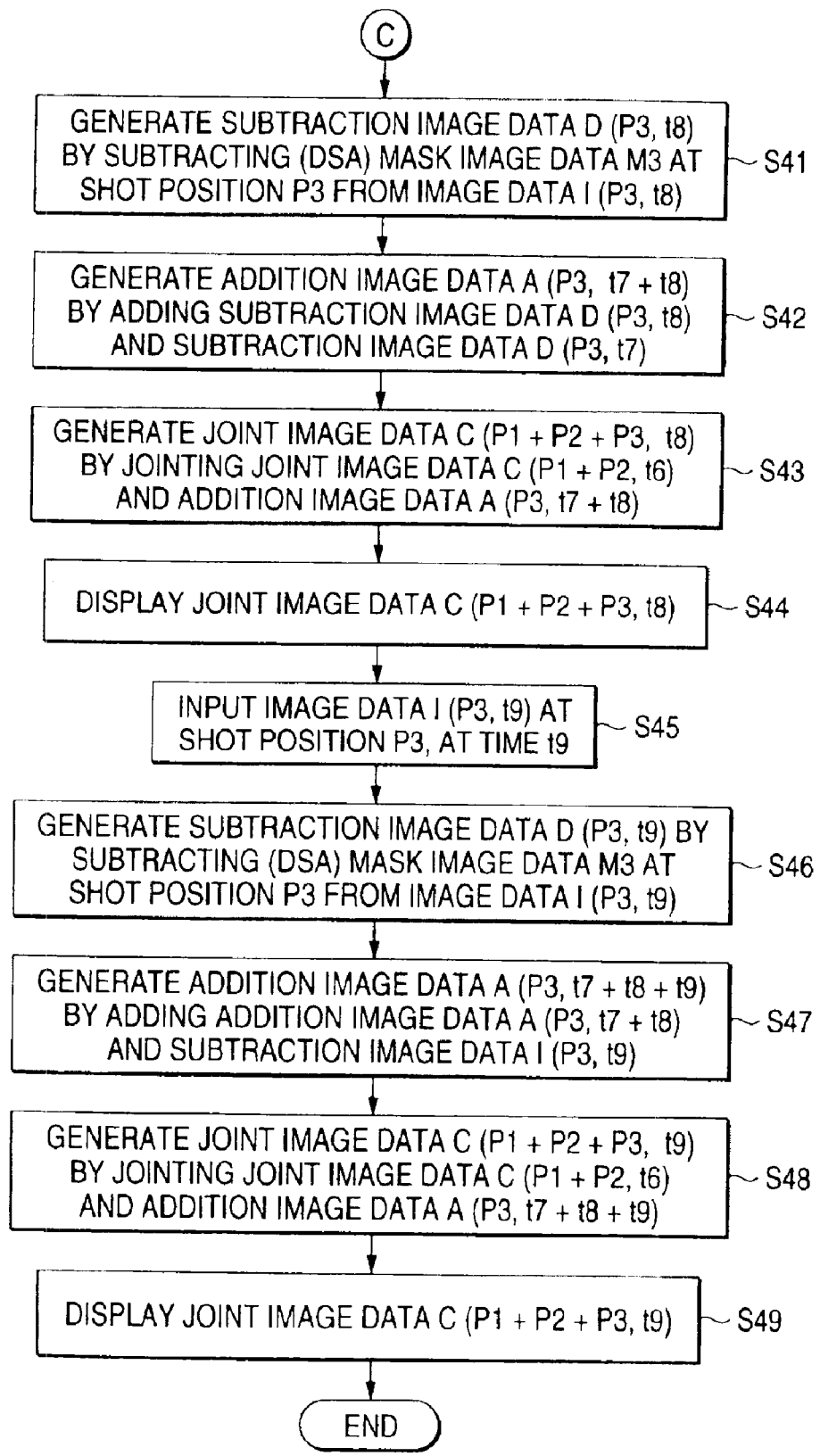
FIG. 8 is a flowchart continuing from FIG. 7.

FIG. 3 is a flowchart detailing the procedure of the shoot operation. FIG. 4A is a plan view showing a plurality of shot positions together with their respective fields of view. FIG. 4B is a side view showing a plurality of shot positions together with their respective fields of view. FIG. 4C shows a shoot sequence of X-rays. The shot position referred to herein is defined as the position of a focal point of the X-ray tube 11 on the Z-axis.

Shot positions P1, P2, and P3 are set, through the input apparatus 70, along the Z-axis at regular intervals with respect to a range to be shot, such as lower legs, wider than the field of view of the imaging system 10 (S1). A distance ΔD between neighboring shot positions (P1 and P2, P2 and P3) is set to a distance longer than the radius R and shorter than the diameter (2·R) of the field of view. Because the distance ΔD between the shot positions is set to a distance longer than the radius R and shorter than the diameter (2·R) of the field of view, the fields of view overlap partially.

The distance between the neighboring shot positions (P1 and P2) and the distance between the neighboring shot positions (P2 and P3) are initially set to an equal distance. However, they may be set to different distances. Meanwhile, the order of shots is set when the shot positions P1, P2, and P3 are set. The order of shots is typically determined according to the flow of the contrast medium (blood), and the order from P1 to P2 to P3 is set herein. It should be noted, however, that the order of shots of the shot positions P1, P2, and P3 may be set arbitrarily.

Then, the number of shots and shot intervals at the respective shot positions P1, P2, and P3 are set through the input apparatus 70 (S2). An equal number of times is set as the number of shots to be taken at the respective shot positions P1, P2, and P3. For example, three times is set for each position. Also, the shot interval ΔT is set to a time obtained by dividing a time width, which begins with the inflow of the contrast medium into the field of view and ends with the outflow of the contrast medium, by (the number of shots −1). The time width differs from region to region and from individual to individual, and is therefore difficult to predict exactly. However, because the shoot method of this embodiment enables compensation for a delay between the predicted time and the actual time, the time width can be a standard value for a region to be shot, derived from the physical constitution or the like of the patient.

When the settings of the shot positions, the number of shots, and the shot intervals are completed, mask images are obtained at the respective shot positions with actual exposure of X-rays in the step prior to injection of the contrast medium (S3). Hereinafter, M1 denotes a mask image obtained at the shot position P1, M2 denotes a mask image obtained at the shot position P2, and M3 denotes a mask image obtained at the shot position P3.

When the preliminary work described as above is completed, a substantial shoot operation is started. Initially, the imaging system 10 is moved and suspended at the first shot position P1 (S4). Then, the contrast medium is actually injected into the patient P (S5). Then, a shot trigger is inputted through the input apparatus 70 at adequate timing. Input timing of the shot trigger may be decided from an elapsed time from the injection of the contrast medium, or alternatively, it may be decided by visual inspection through X-ray fluoroscopy.

Upon input of the shot trigger, shots at the first shot positions P1 are repeated a preset number of times (herein, three times) at the preset shot intervals ΔT (S6). Hereinafter, original image data sets from the shots taken at the shot position P1 at times t1, t2, and t3 are denoted as I (P1, t1), I (P2, t2), and I (P1, t3), respectively.

When the shots at the shot position P1 are completed, the imaging system 10 is moved by the distance ΔD, and suspended at the next shot position P2 (S7). Then, shots at the shot position P2 are repeated a preset number of times (herein, three times) at the preset shot intervals ΔT (S8). Hereinafter, image data sets from the shots taken at the shot position P2 at times t4, t5, and t6 are denoted as I (P2, t4), I (P2, t5), and I (P2, t6), respectively.

When the shots at the shot position P2 are completed, the imaging system 10 is moved by the distance ΔD, and suspended at the last shot position P3 (S9). Then, shots at the shot position P3 are repeated a preset number of times (herein, three times) at the preset shot intervals ΔT (S10). Hereinafter, image data sets from the shots taken at the shot position P3 at times t7, t8, and t9 are denoted as I (P3, t7), I (P3, t8), and I (P3, t9), respectively.

Image processing is performed in the digital imaging processing apparatus 50 in real time in parallel with a series of shots as described above or in non-real time after the shots are taken. Herein, an explanation will be given in a case where image processing is performed in parallel with shots.

Figure 9:
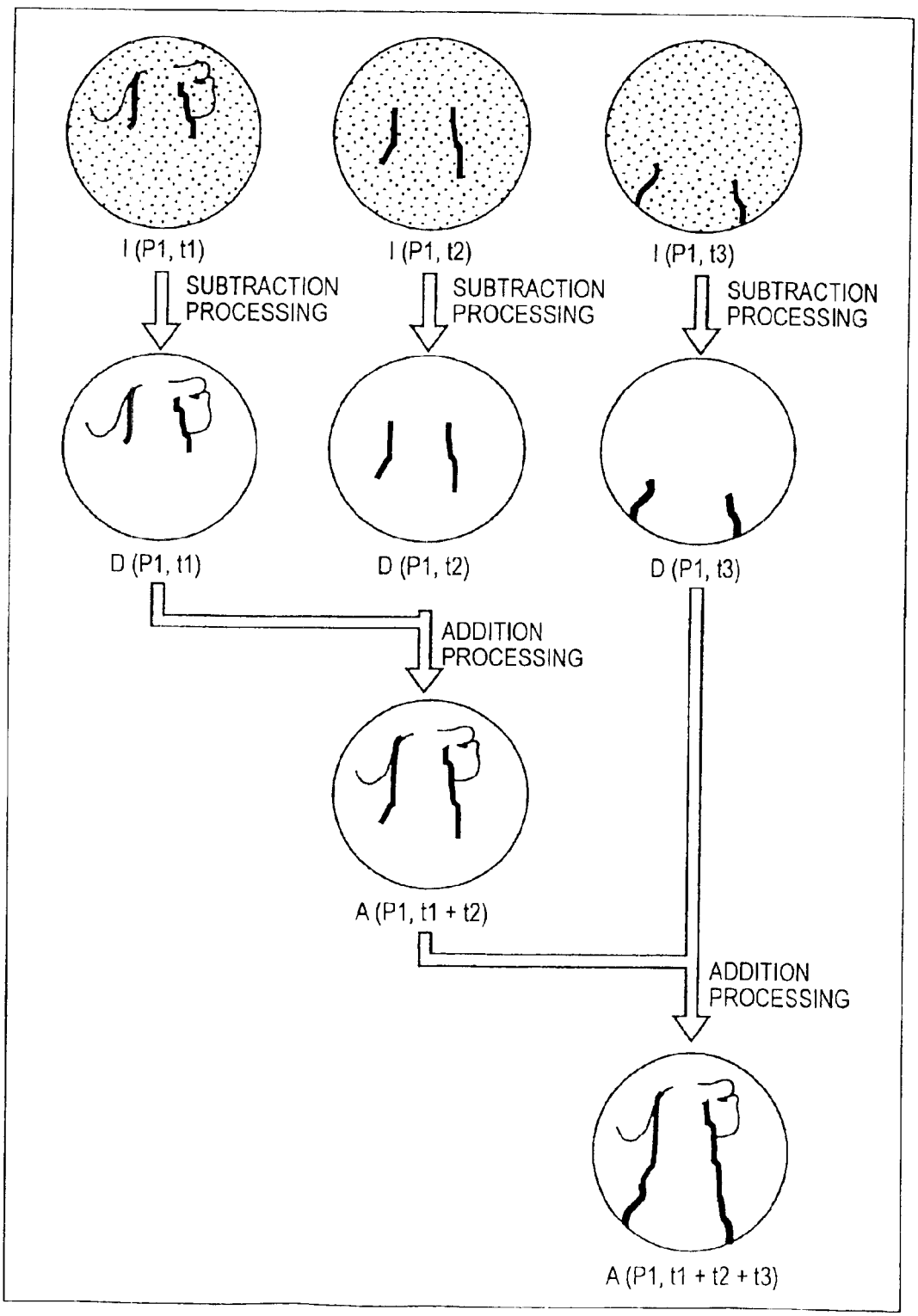
FIG. 9 is an explanatory view of addition processing by the digital image processing apparatus of FIG. 1.
Figure 10:
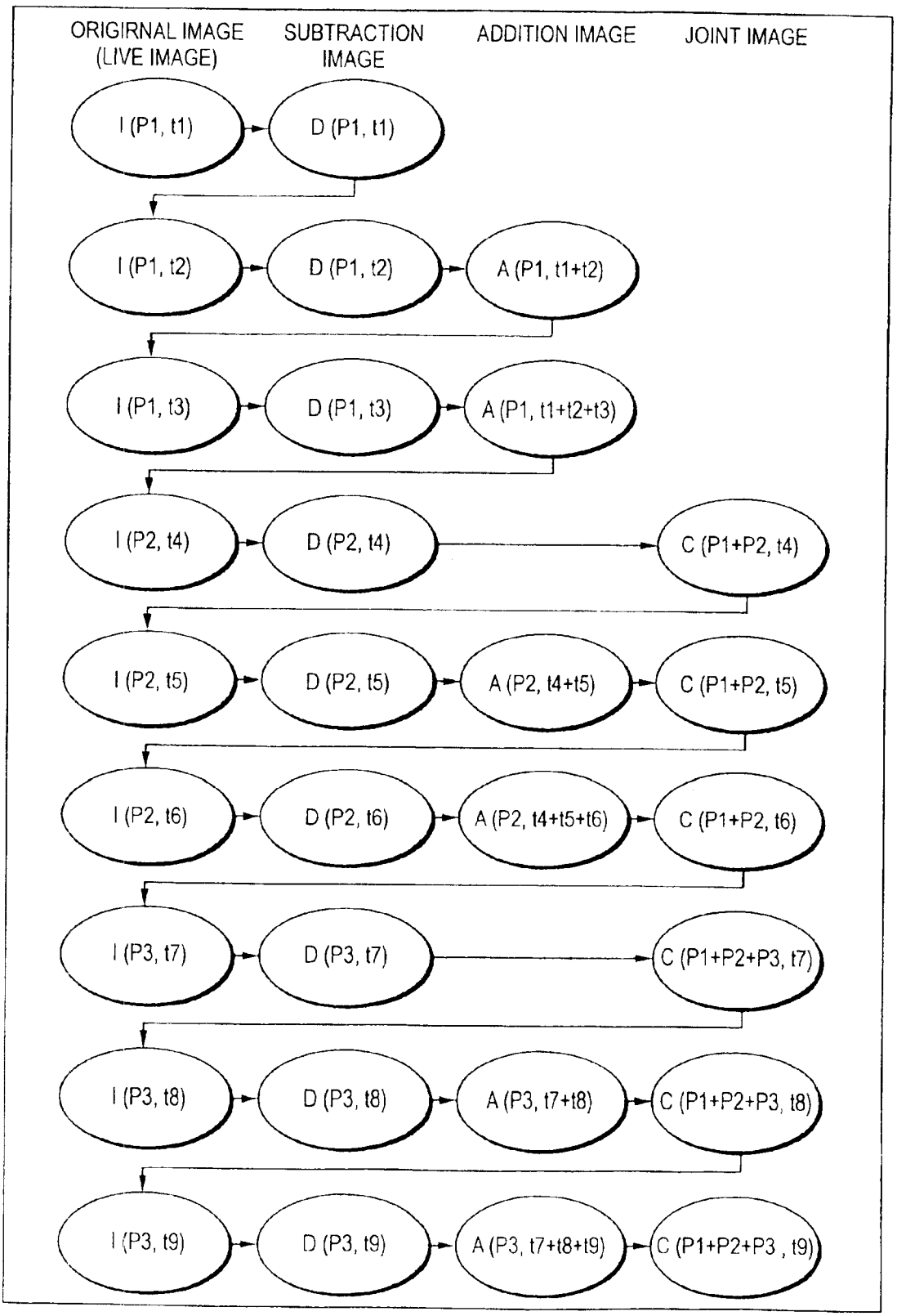
FIG. 10 is a view showing images generated in the digital image processing apparatus of FIG. 1 in the order of generation.
Figure 11:
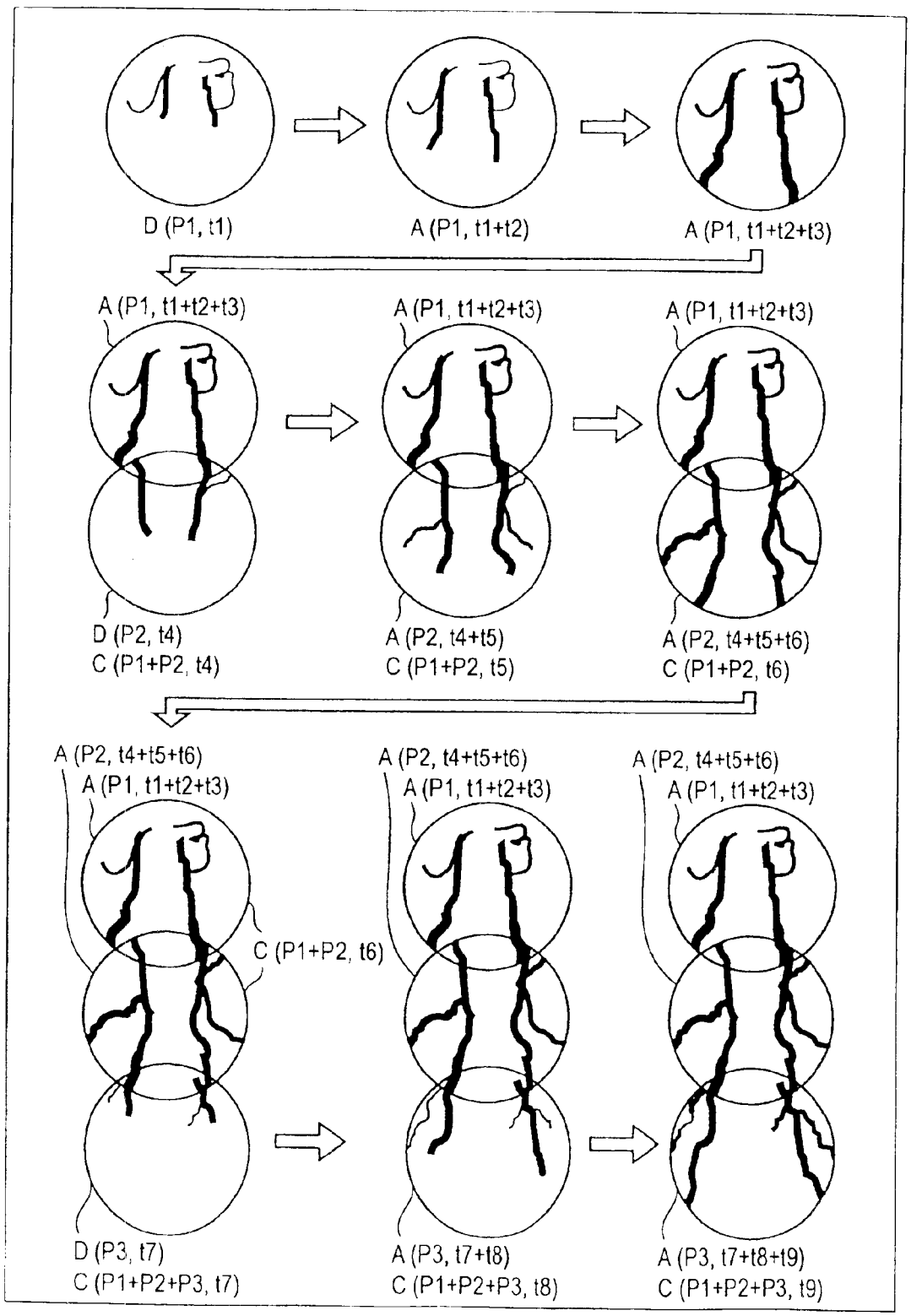
FIG. 11 is a view showing the order of images displayed on an image display apparatus of FIG. 1.

FIG. 5 through FIG. 8 detail the procedure of the image processing by the digital image processing apparatus 50. FIG. 9 schematically shows image processing for the image data sets I (P1, t1), I (P1, t2), and I (P1, t3) from the shots taken at the shot position P1. FIG. 10 shows image data sets generated in the digital image processing apparatus 50 in the order of generation. Further, FIG. 11 shows changes in the image data sets displayed on an image display apparatus 100.

Initially, an original image data set I (P1, t1) from the shot taken at the first time t1 at the first shot position P1 is inputted into the image processing apparatus 50 (S11). In the subtraction processing circuit 55, the mask image M1 obtained at the same shot position P1 is subtracted from the image data set I (P1, t1). Background tissues or the like are thereby removed, and a subtraction image data set D (P1, t1), in which only an image of blood vessels enhanced by the contrast medium is extracted, is generated (S12) and displayed (S13).

Then, an image data set I (P1, t2) obtained at the shot position P1 by a second shot at the time t2 is inputted (S14). In the subtraction processing circuit 55, the mask image M1 at the shot position P1 is subtracted from the image data set I (P1, t2), whereby background tissues or the like are removed, and a subtraction image data set D (P1, t2) is generated, in which only an image of blood vessels enhanced by the contrast medium is extracted (S15). The second subtraction image data set D (P1, t2) is then added to the first subtraction image data set D (P1, t1) between frames in the addition processing circuit 56, and an addition image data set A (P1, t1+t2) is thereby generated (S16) and displayed (S17).

Further, a third shot is taken at the same shot position P1, and an image data set I (P1, t3) is inputted at the time t3

(S18). In the subtraction processing circuit 55, the mask image M1 at the shot position P1 is subtracted from the image data set I (P1, t3), whereby background tissues or the like are removed, and a subtraction image data set D (P1, t3) is generated, in which only an image of blood vessels enhanced by the contrast medium is extracted (S19). The third subtraction image data set D (P1, t3) is added to the addition image data set A (P1, t1+t2) between frames in the addition processing circuit 56, and an addition image data set A(P1, t1+t2+t3) is thereby generated (S20) and displayed (S21).

By repeating shots intermittently at the same position in this manner, and adding up each subtraction image data set, even when a delay in time occurs at each shot timing with respect to the flow of the contrast medium, it is possible to compensate for the delay complementarily. In other words, shot timing at the first shot time t1 is too early for the contrast medium to be distributed across the entire field of view. However, an insufficient distribution of the contrast medium and a low image contrast effect can be compensated for by the subtraction image data sets D (P1, t2) and D (P1, t3) obtained at the second and third shot times t2 and t3, respectively. Conversely, in a case where the shot timing at the last shot time t3 is too late and the contrast medium has already flown out from the field of view, an insufficient distribution of the contrast medium and a low image contrast effect can be compensated for by the subtraction image data sets D (P1, t1) and D (P1, t2) obtained at the first and second shot times t1 and t2, respectively.

Also, by displaying the subtraction image data set D (P1, t1), the addition image data set A (P1, t1+t2), and the addition image data set A (P1, t1+t2+t3) sequentially along the procedure of the shots, it is possible to display a way in which the contrast medium gradually flows in as if it were a moving picture.

Then, processing is performed in the same manner at the shot position P2.

An image data set I (P2, t4) from the shot taken at the first time t4 at the shot position P2 is inputted (S22). In the subtraction processing circuit 55, the mask image M2 at the shot position P2 is subtracted from the image data set I (P2, t4), whereby background tissues or the like are removed, and a subtraction image data set D (P2, t4) is generated, in which only an image of blood vessels enhanced by the contrast medium is extracted (S23).

The final addition image data set A (P1, t1+t2+t3) at the shot position P1 generated in Step S20 is jointed to the subtraction image data set D (P2, t4) in the joint processing circuit 58 based on the shot position data sets at P1 and P2, and a joint image data set C (P1+P2, t4) is thereby generated (S24) and displayed (S25).

Then, an image data set I (P2, t5) obtained at the time t5 by a second shot at the same shot position P2 is inputted (S26). In the subtraction processing circuit 55, the mask image M2 is subtracted from the image data set I (P2, t5), and a subtraction image data set D (P2, t5) is thereby generated (S27). The second subtraction image data set D (P2, t5) at P2 is added to the first subtraction image data set D (P2, t4) in the addition processing circuit 56 between frames, and an addition image data set A (P2, t4+t5) is thereby generated (S28).

Then, the final addition image data set A (P1, t1+t2+t3) at the shot position P1 generated in Step S20 is jointed to the addition image data set A (P2, t4+t5) in the joint processing circuit 58 based on the shot position data sets at P1 and P2, and a joint image data set C (P1+P2, t5) is thereby generated (S29) and displayed (S30).

Then, an image data set I (P2, t6) obtained at the time t6 by a third shot at the same shot position P2 is inputted (S31). In the subtraction processing circuit 55, the mask image M2 is subtracted from the image data set I (P2, t6), and a subtraction image data set D (P2, t6) is thereby generated (S32). The third subtraction image data set D (P2, t6) at P2 is added to the addition image data set A (P2, t4+t5) in the addition processing circuit 56 between frames, and an addition image data set A (P2, t4+t5+t6) is thereby generated (S33).

Then, the final addition image data set A (P1, t1+t2+t3) at the shot position P1 generated in Step S20 is jointed to the addition image data set A (P2, t4+t5+t6) in the joint processing circuit 58 based on the shot position data sets at P1 and P2, and a joint image data set C (P1+P2, t6) is thereby generated (S34) and displayed (S35).

Then, processing is performed in the same manner at the shot position P3.

An image data set I (P3, t7) from the shot taken at the first time t7 at the shot position P3 is inputted (S36). In the subtraction processing circuit 55, the mask image M3 at the shot position P3 is subtracted from the image data set I (P3, t7), whereby background tissues or the like are removed, and a subtraction image data set D (P3, t7) is generated, in which only an image of blood vessels enhanced by the contrast medium is extracted (S37).

The final joint image data set C (P1+P2, t6) at the shot position P2 is jointed to the subtraction image data set D (P3, t7) in the joint processing circuit 58 based on the shot position data sets at P1, P2, and P3, and a joint image data set C (P1+P2+P3, t7) is thereby generated (S38) and displayed (S39).

Then, an image data set I (P3, t8) obtained at the time t8 by a second shot at the same shot position P3 is inputted (S40). In the subtraction processing circuit 55, the mask image M3 is subtracted from the image data set I (P3, t8), and a subtraction image data set D (P3, t8) is thereby generated (S41). The second subtraction image data set D (P3, t8) at P3 is added to the first subtraction image data set D (P3, t7) at P3 in the addition processing circuit 56 between frames, and an addition image data set A (P3, t7+t8) is thereby generated (S42).

Then, the final joint image data set C (P1+P2, t6) at the shot position P2 is jointed to the addition image data set A(P3, t7+t8) in the joint processing circuit 58 based on the shot position data sets at P1, P2, and P3, and a joint image data set C (P1+P2+P3, t8) is thereby generated (S43) and displayed (S44).

Then, an image data set I (P3, t9) obtained at the time t9 by a third shot at the same shot position P3 is inputted (S45). In the subtraction processing circuit 55, the mask image M3 is subtracted from the image data set I (P3, t9), and a subtraction image data set D (P3, t9) is thereby generated (S46). The third subtraction image data set D (P3, t9) at P3 is added to the addition image data set A (P3, t7+t8) in the addition processing circuit 56 between frames, and an addition image data set A (P3, t7+t8+t9) is thereby generated (S47).

Then, the final joint image data set C (P1+P2, t6) at the shot position P2 is jointed to the addition image data set A (P3, t7+t8+t9) in the joint processing circuit 58 based on the shot position data sets at P1, P2, and P3, and a joint image data set C (P1+P2+P3, t9) is thereby generated (S48) and displayed (S49).

As has been described, by repeating shots intermittently at each of a plurality of shot positions having partially overlapped fields of view and adding up each subtraction image data set, even when the density in contrast is too low at each shot timing due to a delay in time with respect to the flow of the contrast medium, it is possible to obtain adequate density in contrast by compensating for the delay complimentarily.

Also, by cumulatively adding up images generated successively through intermittent repetitive shots and displaying resulting images sequentially, it is possible to display a way in which the contrast medium gradually flows in as if it were a moving picture.

Further, by jointing images obtained by moving shot positions spatially, it is possible to display a way in which the contrast medium gradually flows in across an extensive range as if it were a moving picture.

Figure 12:
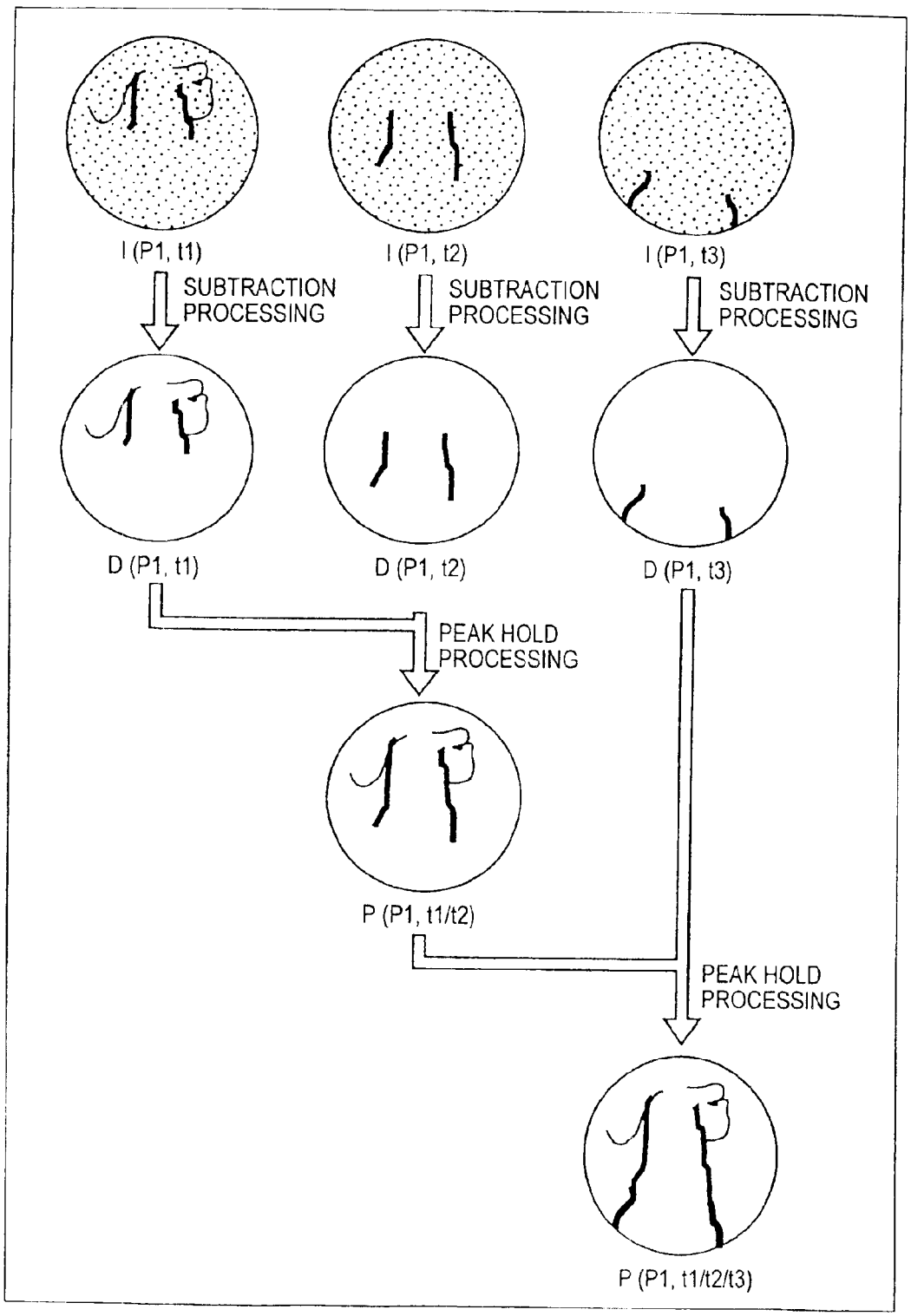
FIG. 12 is an explanatory view of peak hold processing by the digital image processing apparatus of FIG. 1.

FIG. 12 shows image processing in a case where peak hold processing is selected instead of the addition processing described above. According to the addition processing, the density in contrast is increased with the number of additions. This may cause unevenness in the density in contrast within a single image. The peak hold processing has an advantage in that unevenness in the density in contrast can be reduced.

The higher pixel value is selected for each pixel between the subtraction image data set D (P1, t1) from the original image data set I (P1, t1) from the shot taken at the first shot time t1 at the first shot position P1 and the subtraction image data set D (P1, t2) from the original image data set I (P1, t2) from the shot taken at the same shot position P1 at the time t2. A peak hold image data set P (P1, t1/t2), which indicates a distribution of high pixel values, is thereby generated.

The peak hold processing is performed between the subtraction image data set D (P1, t3) from the original image data set I (P1, t3) from the shot taken at the next time t3 and the peak hold image data set P (P1, t1/t2) generated earlier. A peak hold image data set P (P1, t1/t2/t3), which indicates a distribution of high pixel values, is thereby generated.

According to the peak hold processing, the pixel values are not added up, and instead any one of the pixel values is merely selected from a plurality of images taken at different shot times. Hence, the original pixel values can be maintained and abrupt increment in the density in contrast due to additions can be eliminated. Also, according to the peak hold processing, because the pixel having the highest pixel value is selected from a plurality of images taken at the different shot times for all the individual pixels, all the paths in which the contrast medium has flown from the time t1 to the time t3 are not erased and left on the image. A delay in shot timing can be thus compensated for as was with the addition processing.

Figure 13:
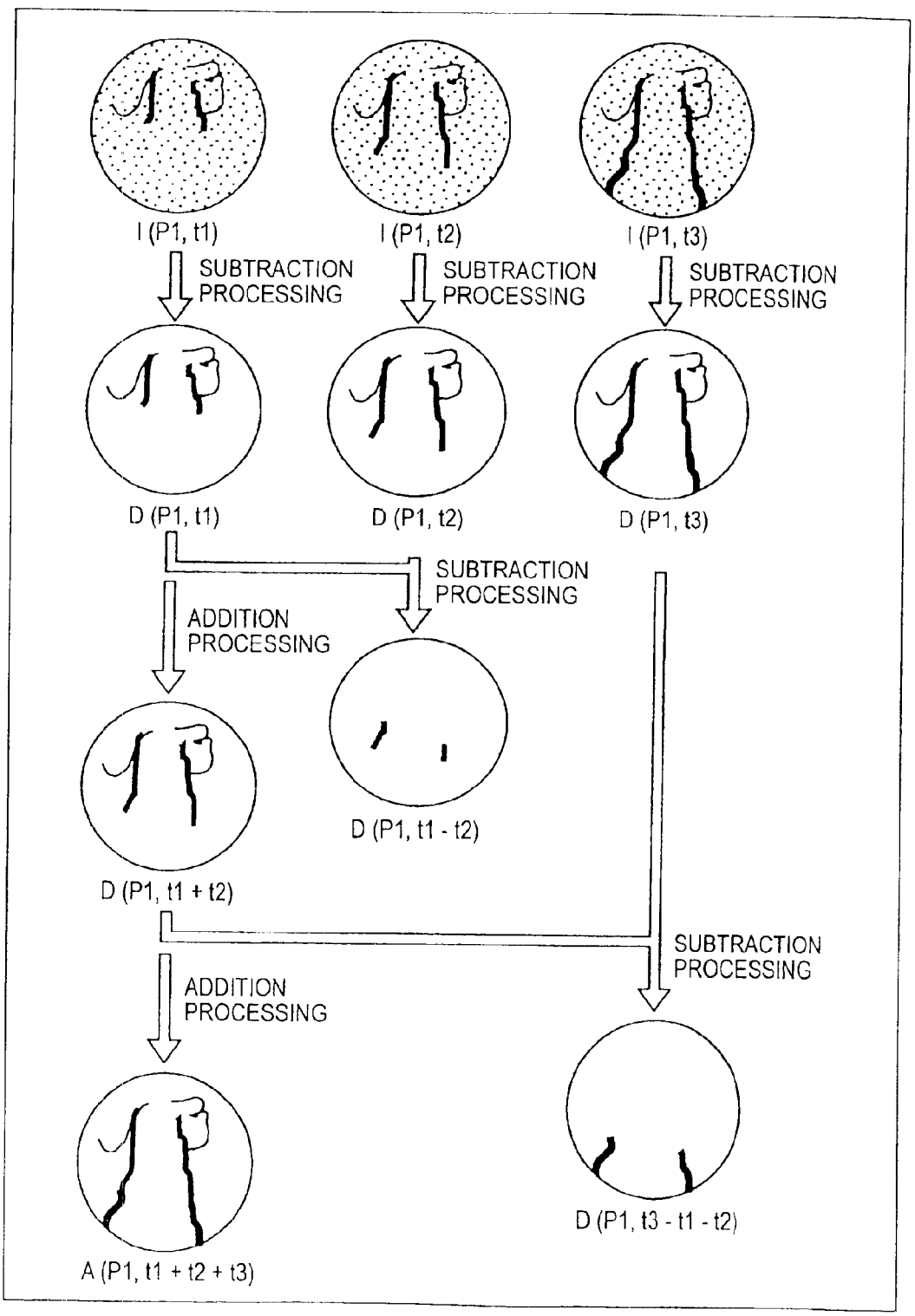
FIG. 13 is an explanatory view of subtraction and addition processing by the digital image processing apparatus of FIG. 1.
Figure 14:
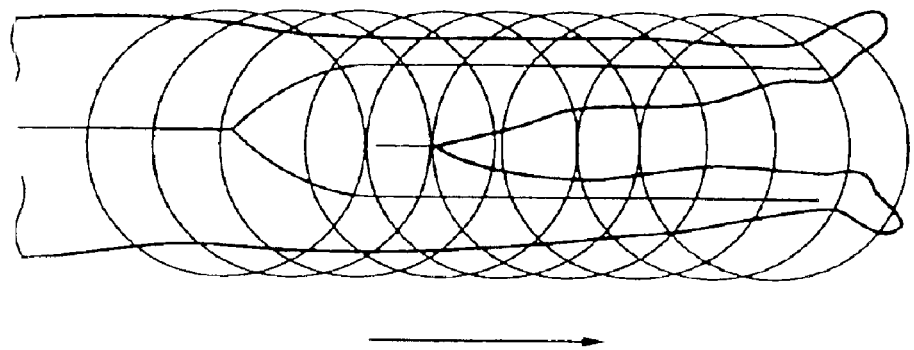
FIG. 14 is an explanatory view of a conventional bolus-chasing shoot method.

Besides the peak hold processing, a method of performing the subtraction processing together with the addition processing is known as a method of reducing unevenness in density. This method is suitable to an injection method by which the contrast medium is injected little by little over an extensive time rather than the bolus injection. The procedure is detailed in FIG. 13. The subtraction image data set D (P1, t1) from the original image data set I (P1, t1) from the shot taken at the first shot time t1 at the first shot position P1 is subtracted from the subtraction image data set D (P1, t2) from the original image data set I (P1, t2) from the shot taken at the same shot position P1 at the time t2. A subtraction image data set D (P1, t2−t1) is thereby generated, in which a portion newly extended from the time t1 to time t2 is extracted. The subtraction image data set D (P1, t2−t1) is added to the first subtraction image data set D (P1, t1).

Likewise, the subtraction image data set D (P1, t2−t1) obtained earlier is subtracted from the subtraction image data set D (P1, t3) from the original image data set I (P1, t3) from the third shot at the third time t3. A subtraction image data set D (P1, t3−t2−t1) is thereby generated, in which a portion newly extended from the time t2 to time t3 is extracted. The subtraction image data set D (P1, t3−t2−t1) is added to the subtraction image data set D (P1, t2−t1) obtained earlier.

By performing the subtraction processing together with the addition processing in this manner, a newly extended region alone is added up cumulatively. Hence, the original pixel values are maintained, and abrupt increment in the density in contrast due to additions can be eliminated. Moreover, all the paths in which the contrast medium has flown from the time t1 to time t3 are not erased and left on the image. Hence, a delay in shot timing can be compensated for as was with the addition processing.

(Modification)

The invention is not limited to the embodiment described above, and can be modified in various manners without departing from the gist of the invention when reduced to practice. Further, the embodiment above includes various steps, and various inventions can be extracted by adequately combining a plurality of constituent features disclosed in the embodiment. For example, of all the constituent features disclosed in the embodiment, some of the constituent features may be omitted.

According to the invention, it is possible to provide an X-ray diagnostic apparatus that can tolerate a delay in shot timing.

What is claimed is:

1. An X-ray diagnostic apparatus, comprising:
an imaging system configured to generate image data sets from shots by subjecting a patient to X-ray exposure;
a supporting mechanism configured to support said imaging system in such a manner so as to be allowed to move relatively with respect to said patient;
a system controller configured to control said imaging system and said supporting mechanism in such a manner that shots are repeated at each of a plurality of shot positions set discretely along a body axis of said patient; and
an image processing unit configured to generate a given image data set covering a range wider than a field of view of said imaging system from said image data sets, comprising,
an addition processing unit configured to add up said image data sets at a same shot position and thereby generates an addition image data set, and
a joint processing unit configured to generate said given image data set by jointing said addition image data sets at different shot positions.

2. The X-ray diagnostic apparatus according to claim 1, wherein said image processing unit is configured to generate said given image data set comprising one of a blood vessel extracted image data set and a blood vessel enhanced image data set.

3. The X-ray diagnostic apparatus according to claim 1, wherein said image processing unit includes a subtraction processing unit configured to subtract corresponding mask image data sets from said image data sets.

4. The X-ray diagnostic apparatus according to claim 1, wherein said system controller is configured to align said plurality of shot positions at a regular pitch, and the pitch is longer than a radius of the field of view of said imaging system and shorter than a diameter of the field of view of said imaging system.

5. The X-ray diagnostic apparatus according to claim 1, wherein said system controller is configured to repeat shots a predetermined number of times at each of said plurality of shot positions.

6. The X-ray diagnostic apparatus according to claim 1, wherein said image processing unit includes a peak hold processing unit configured to generate a peak hold image data set from said image data sets at a same shot position.

7. The X-ray diagnostic apparatus according to claim 6, wherein said image processing unit includes a joint processing unit configured to generate said given image data set by jointing said peak hold image data sets at different shot positions.

8. An X-ray diagnostic apparatus, comprising:
- an imaging system configured to generate image data set from shots by subjecting a patient to X-ray exposure;
- a supporting mechanism configured to support said imaging system in such a manner so as to be allowed to move relatively with respect to said patient;
- a system controller configured to control said supporting mechanism in such a manner that said imaging system is repetitively moved and suspended in turn along a body axis of said patient, and to control said imaging system in such a manner that shots are repeated at each suspended position; and
- an image processing unit configured to generate a given image data set covering a range wider than a field of view of said imaging system from said image data sets, comprising,
  - a subtraction unit configured to subtract corresponding mask image data sets from said image data sets,
  - an addition processing unit configured to generate an addition image data set by adding up said image data sets at a same shot position, and
  - a joint processing unit configured to generate said given image data set by jointing said addition image data sets at different shot positions.

9. The X-ray diagnostic apparatus according to claim 8, wherein said image processing unit comprises:
- a peak hold processing unit configured to generate a peak hold image data set from said image data sets at a same shot position; and
- a joint processing unit configured to generate said given image data set by jointing said peak hold image data sets at different shot positions.

10. The X-ray diagnostic apparatus according to claim 8, wherein said system controller is configured to move said imaging system by a movement unit that is longer than a radius of the field of view of said imaging system and shorter than a diameter of the field of view of said imaging system.

11. The X-ray diagnostic apparatus according to claim 8, wherein said system controller is configured to repeat shots an equal number of times at each suspended position.

12. An X-ray diagnostic apparatus, comprising:
- an imaging system configured to generate image data sets from shots by subjecting a patient to X-ray exposure;
- a supporting mechanism configured to generate said imaging system in such a manner so as to be allowed to move relatively with respect to said patient;
- a system controller configured to control said imaging system and said supporting mechanism so as to generate a plurality of first image data sets at different shot times, all corresponding to a first shot position, and a plurality of second image data sets at different shot times, all corresponding to a second shot position; and
- an image processing unit configured to generate a single third image data set covering a range wider than a field of view of said imaging system from said first and second image data sets, comprising,
  - a subtraction unit configured to subtract corresponding mask image data sets from said image data sets,
  - an addition processing unit configured to generate an addition image data set by adding up said image data sets at a same shot position, and
  - a joint processing unit configured to generate said given image data set by jointing said addition image data sets at different shot positions.

13. The X-ray diagnostic apparatus according to claim 12, wherein
- said addition processing unit configured to generate a single first addition image data set by adding up said plurality of first image data sets and to generate a single second addition image data set by adding up said plurality of second image data sets; and
- said joint processing unit configured to generate said third image data set by jointing said first addition image data set and said second a addition image data set according to the first and second shot positions.

14. The X-ray diagnostic apparatus according to claim 12, wherein said image processing unit comprises:
- a peak hold processing unit configured to generate a single first peak hold image data set from said plurality of first image data sets and to generate a single peak hold image data set from said plurality of second image data sets; and
- the joint processing unit is configured to generate said third image data set by jointing said first peak hold image data set and said second peak hold image data set according to the first and second shot positions.

* * * * *